United States Patent [19]

Clausen et al.

[11] Patent Number: 5,674,476
[45] Date of Patent: Oct. 7, 1997

[54] PROCESS FOR MAKING A PERSULFATE-CONTAINING GRANULATE FOR DECOLORIZING OR BLEACHING HAIR

[75] Inventors: Thomas Clausen; Wolfgang R. Balzer, both of Alsbach; Volker Port, Dieburg; Jolanthe Kujawa, Darmstadt, all of Germany

[73] Assignee: Wella Aktiengesellschaft, Darmstadt, Germany

[21] Appl. No.: 612,533

[22] Filed: Mar. 8, 1996

Related U.S. Application Data

[62] Division of Ser. No. 323,547, Oct. 17, 1994, abandoned.

[30] Foreign Application Priority Data

Oct. 30, 1993 [DE] Germany .................. 43 37 178.7

[51] Int. Cl.$^6$ ........................................... A61K 7/135
[52] U.S. Cl. ........................... 424/62; 424/70.1; 424/501
[58] Field of Search ........................... 424/62, 70.1, 501

[56] References Cited

U.S. PATENT DOCUMENTS

| 3,726,967 | 4/1973 | Vorsatz et al. ............... 424/62 |
| 5,279,313 | 1/1994 | Clausen et al. ............... 132/208 |
| 5,298,240 | 3/1994 | Schroeder et al. ............. 424/70 |
| 5,380,340 | 1/1995 | Neunhoeffer et al. .......... 8/409 |

FOREIGN PATENT DOCUMENTS

| 2023922 | 2/1978 | Germany . |
| 4026235 | 2/1992 | Germany . |

*Primary Examiner*—Jyothsna Venkat
*Attorney, Agent, or Firm*—Michael J. Striker

[57] ABSTRACT

The method of making a granulate composition for decolorizing or bleaching hair consists of preparing a powdery mixture consisting of from 30 to 65% by weight of one or more inorganic persulfates, from 1 to 20% by weight of a binding agent selected from the group consisting of polyvinylpyrrolidone and polyethylene glycols having molecular weights of 200 to 10,000; of 15 to 45% by weight of at least one salt selected from the group consisting of alkali metal carbonates, alkaline earth metal carbonates, alkali metal hydrogen carbonates, alkali metal silicates and from 0.1 to 3 percent by weight of a chelating agent, and one or more auxiliary and additive substance selected from the group consisting of perfume oils, hair dyes, amphoteric, anionic, cationic and nonionic surface-active substances and water-soluble thickeners; after making this powdery mixture, spraying ethanol and/or isopropanol in a weight ratio from 13:1 to 4:1 (powdery mixture to alcohol) into the powdery mixture to form a moistened mixture; granulating the moistened mixture formed during the spraying in a granulating apparatus to form a moist granulate; and after the granulating, drying the moist granulate to remove the alcohol or alcohols and to form the granulate composition.

6 Claims, No Drawings

PROCESS FOR MAKING A PERSULFATE-CONTAINING GRANULATE FOR DECOLORIZING OR BLEACHING HAIR

This application is a continuation of application Ser. No. 08/323,547, filed Oct. 17, 1994 now abandoned.

BACKGROUND OF THE INVENTION

The present invention relates to a process for making a persulfate-containing composition in granulate form for decolorizing or bleaching hair and the granulate composition made by that process.

For decolorizing or bleaching hair standard oxidizing preparations are employed which are obtained by dissolving a so-called bleaching powder (powder mixture of alkali metal salts and inorganic persalts such as sodium or ammonium persulfate) in an aqueous hydrogen peroxide solution.

The use of this type of bleaching powder, which necessarily comprises several components, is accompanied by several disadvantages. Thus separation of different powder components frequently occurs during transport or storage due to the presence of and use of raw materials having different densities during transport or storage. The heavier powder components collect in the lower part, while the lighter powder components collect in the upper part of the powder. This separation has the effect that different portions of the same batch of powder taken from different locations in the batch have different chemical compositions and thus also provide a different bleaching effect.

To avoid this separation effect it is necessary to shake or stir the batch of powder prior to taking the powder portion from the powder which however cannot usually be done by the user.

This type of separation can also be prevented using powder mixture with very small grain size. This has the disadvantage however that this type of powdery mixture—particularly on opening of the container during removal of powder or on mixing with hydrogen peroxide solution—is inclined to form copious amounts of dust, which can lead to irritation of the lungs. Furthermore this type of powdery mixture has a comparatively large surface area because of the reduced grain size, whereby adsorption of moisture is promoted on opening and closing of the container so that a reduction in the bleaching action of the preparation occurs because of the deactivation of the oxygen carrier.

Numerous attempts have already been made to solve this problem.

Thus a mixture including a granulate of inorganic persulfate and a granulate of conventional ingredients of bleaching agents is used instead of bleaching powder in the method described in German Patent Application DE-OS 40 26 235. Of course the dust generation problem can be eliminated by this method but the problem of separation can not be solved in this manner, since it is extremely difficult to make individual granules which are identical to keep the grain size or bulk density constant. An impairment of the bleaching effect can occur because of the differing solubilities of the individual granulates. From an economic standpoint it is worse to make a mixture of individual granulates than a single granulate.

German Published Patent Application DE-AS 20 23 922 recommends using a granulate instead of a powder. This granulate is made by the spraying of a bleaching powder containing all the required components with an aqueous, alcoholic or aqueous-alcoholic polymer solution in a suitable mixer.

This granulating process however leads to a considerably loss of ammonia, whereby the bleaching effect of the preparation is considerably impaired. This ammonia loss can be compensated by the increase of the amount of ammonium salt used in the powder and/or by addition of ammonia to the polymer solution. Since the ammonia loss fluctuates strongly in this granulating process it is not possible to make a granulate with a constant chemical composition.

The above-described granulating process has also two additional disadvantages: First, the preparation of a homogeneous, sprayable binding agent solution having a predetermined viscosity is very time-consuming. Second for the introduction of the required amount of binding agent a relatively large amount of polymer solution (ratio of powder : polymer solution=1:1) is required, which appears to be doubtful from both an economic and ecologic point of view—particularly using an alcoholic solution, since a high energy consumption for drying the granulates and/or the recovery of the alcohol used is required.

Also the granulate made according to this process are very hard and dispersible only with difficulty in hydrogen peroxide solution.

SUMMARY OF THE INVENTION

It is an object of the present invention to provide a suitable granulate composition for decolorizing or bleaching hair and a method of making the granulate composition, which avoids the above-described disadvantages.

It is also an object of the invention to provide a composition for decolorizing or bleaching hair consisting of a mixture of a hydrogenperoxide preparation and the granulate composition.

It has been found surprisingly that the above-described disadvantages can be avoided when the binding agent is worked into the bleaching powder during the granulation of the bleaching powder when the mixture of the binding agent and the bleaching powder is subsequently sprayed with a suitable solvent.

According to the invention a process for making a granulate composition for decolorizing or bleaching of hair comprises the steps of spraying of a powdery mixture containing a binding agent, at least one inorganic persulfate and at least one conventional auxiliary and additive substance with an alcohol in apparatus at room temperature and subsequently drying the granulate composition formed thereby.

In the process according to the invention first the powdery mixture is made by mixing the inorganic persulfate with the conventional auxiliary and additive materials and binding agent. Commercial mixers, e.g. mixers operating according to the Diosna-System or Plowshare mixers, can be used.

Then this powdery mixture is moistened with alcohol by agitation in a suitable granulation apparatus (e.g. the above-described mixers or granulating drum). A predetermined alcohol quantity is used so that a moistened mixture still not inclined to agglomerate arises.

In a preferred embodiment of the method the weight ratio of powdery mixture to alcohol amounts to advantageously 13:1 to 4:1, but a weight ratio of 10:1 to 7:1 is particularly preferred.

A moderately volatile alcohol, whose boiling point is not over about 85° C. and in which the binding agent is sufficiently soluble, can be used as the alcohol in the method according to the invention. Ethanol, isopropanol or a mixture thereof are particularly preferred as the alcohol to be used in the method.

Polyethyleneglycols with a molecular weight of 200 to 10000, advantageously 200 to 600, or polyvinylpyrrolidone can be used as the binding agent.

The binding agent is used in the powdery mixture in an amount of 1 to 20 percent by weight, advantageously 3 to 8 percent by weight.

Besides the binding agent the powdery mixture contains one or more inorganic persulfates, such as sodium persulfate, potassium persulfate or ammonium persulfate. The persulfates used in the mixture are advantageously present in an amount of 30 to 65 percent by weight, particularly 40 to 60 percent by weight.

Furthermore the powdery mixture can contain alkaline reacting alkali metal or alkaline earth metal salts, such as sodium carbonate, sodium silicate, sodium hydrogen carbonate or magnesium carbonate and in preferred embodiments in amounts of 15 to 45 percent by weight, particularly of 25 to 40 percent by weight.

Preferred embodiments of the powdery mixture can also contain chelating reagents for heavy metals, e.g. salts of ethylenediaminetetraacetic acid, in concentrations of 0.1 to 3 percent by weight, advantageously 0.5 to 1.5 percent by weight, as well as perfumes and hair dye compounds, for example, selected from the classes of Ultramarine dyes and acidic dyes, usually in an amount of up to 1 percent by weight.

Similarly the preferred embodiments of the granulate composition or powdery mixture according to the invention can contain other conventional auxiliary and additve substance selected from the group consisting of wetting agents and emulsifiers in powdery form from the classes of amphoteric, anionic, cationic or nonionic surface-active substances, such as alkylbetaines, fatty alcohol sulfates, fatty alcohol ether sulfates, alkyl sulfates, alkyl benzene sulfonates, alkyl trimethylammonium salts, ethoxylated fatty alcohols, ethoxylated nonylphenols, ethoxylated fatty acid esters and fatty acid alkanolamides, as well as water soluble thickeners, especially starches or cellulose ethers, such as methyl cellulose, ethyl cellulose, methylhydroxyethyl cellulose, methylhydroxyethyl cellulose, methylhydroxypropylcelllulose and carboxymethyl cellulose. The wetting agents and emulsifiers can be contained in amounts of 0.1 to 15 percent by weight, advantageously 0.1 to 8 percent by weight, while the amounts of the water-soluble thickeners in included in amounts of 0.1 to 15 percent by weight, advantageously 1 to 10 percent by weight.

The above-described powdery mixture is then treated in a suitable granulating apparatus until the granulate composition is formed. The granulating time depends essentially on the granulation method used. Usually the granulation requires from about 10 to 60 minutes. The mixing granulation requires from about 10 to 20 minutes, while the fluidized bed granulation which is characterized by longer spraying times requires granulation times from about 20 to 60 minutes.

After ending of the granulating process the granulate is dried in a suitable drier, e.g. a shelf drier, a drum drier, a fluidized bed drier or a vacuum drier, with heat or in vacuum. A heating of the granulate to temperatures over 40° C. can be avoided.

After finishing the drying process the alcohol content of the granulate should be less than 1 percent by weight.

The diameter of the granules or individual grains obtained is in the vicinity of 0.1 to 2 mm, especially from 0.2 to 0.5 mm.

The unwanted fractions of fine and coarse grained granulate can be separated from the product by sieving out with calibrated sieves so that an optimum grain size spectrum remains in the product for the particular application at hand.

The separated fine and coarse grain fractions can be fed back again to the process for making the composition according to the invention.

The granulate composition made by the process according to the invention in contrast to the method according to the state of the prior art has an easy dosability, an improved homogeneity and an improved dispersibility in hydrogen peroxide solution. The granulate composition according to the invention can be used without production of dust and has a constant chemical composition. A more uniform and considerably improved bleaching action in comparison to the state of the art is provided by the granulate composition according to the invention.

The granulate composition is mixed with a hydrogen peroxide preparation in weight ratios of about 1:1 to 1:3, preferably weight ratios of 1:1.5 to 1:2, to form a mixture or composition for application to the hair to bleach or decolorize it.

The aqueous hydrogen peroxide preparation contains about 4 to 18 percent by weight, advantageously about 6 to 12 percent by weight hydrogen peroxide, and, if necessary, for preparations of this type standard or conventional additive substances, such as perfume oils, hair dyes, stabilizers, wetting agents and emulsifiers.

The application of the composition for decolorizing or bleaching of hair occurs in the standard way, in which 20 to 40 grams, advantageously 30 grams, according to hair length, of the granulate composition made by the method according to the invention are mixed directly prior to use with the hydrogen peroxide preparation in a weight ratio (granulate composition to hydrogen peroxide) of 1:1 to 1:3, advantageously 1:1.5 to 1:2, to obtain the composition or mixture for bleaching or decolorizing hair; the mixture is applied directly to the hair and, after an acting time of 15 to 60 minutes, is rinsed again from the hair.

The subject matter of the invention is now illustrated in greater detail but without additional limitation by the following examples.

EXAMPLES

Example 1

Preparation process 15 kg of the following powdery mixture are granulated at room temperature by spraying with 2.25 kg (corresponding to 2.9 l) of isopropanol in a Plowshare mixture, Model FM 50, of the Lodge Brothers(Firma Gebrüder Lödige).

Powdery Mixture 400 g potassium persulfate 100 g ammonium persulfate 200 g sodium silicate 110 g magnesium carbonate 80 g sodium stearate 60 g polyvinyl pyrrolidone 37 g carboxymethyl cellulose 10 g sodium methylene diamino tetraacetate (EDTA)

3 g perfume 1000 g

After ending the granulation (granulation time: 10 minutes) the granulate composition obtained is dried in a fluidized bed drier, Model GPCG 3, of the Glatt Firm (drying time: 25 minutes). The input air temperature amounts to about 60° C. and the granulate is not heated over 40° C.

The granulate so obtained is characterized by a high abrasion resistance, a good dispersibility, a constant chemical composition and an outstanding bleaching action.

Example 2

Preparation process 15 kg of the following powder mixture, 300 g potassium persulfate 190 g ammonium persulfate 220 g sodium silicate 110 g magnesium carbonate 80 g sodium stearate 60 g polyvinyl pyrrolidone 30 g carboxymethyl cellulose 10 g sodium methylene diaminotetraacetate (EDTA)

1000 g, are granulated and dried in the same way as in example 1 by spraying with 2.1 kg (corresponding to 2.7 l) of isopropanol.

A granulate is obtained with a grain size distribution between 0.15 and 1.2 mm.

Example 3

Comparative Example

A bleaching agent, which was made by mixing 10 g of the granulate composition according to example 1 and/or example 2 with 15 g of a 9 percent hydrogen peroxide solution, was compared in regard to its bleaching properties with an agent according to German Patent Application DE-AS 2 023 922, which was made by mixing of 10 g of the granulate composition described in the following section with 15 g of a 9 percent by weight hydrogen peroxide solution.

Granulate according to German Patent Application DE-AS 20 23 922

14.1 kg of the following powder, 400 g potassium persulfate 100 g ammonium persulfate 200 g sodium silicate 110 g magnesium carbonate 80 g sodium stearate 37 g carboxymethyl cellulose 10 g sodium ethylene diaminotetraacetate (EDTA)

3 g perfume 940 g of powder, was granulated by spraying with a solution of 0.9 kg polyvinylpyrrolidone in 13.2 kg of isopropanol at room temperature in a Plowshare mixer, Model FM 50, of the Firm Gebrüder Lödige(Lodge Brothers).

The granulate composition so obtained is extraordinarily hard and large-grained and is only dispersed with difficulty in hydrogen peroxide solution.

The three bleaching agents or composition for bleaching hair obtained (Nr. 1: granulate composition according to Example 1; Nr. 2: granulate composition according to Example 2; and Nr. 3 granulate composition according to German Patent Application 20 23 922) were separately applied to different brown natural hair strands. Subsequently the hair strands so treated were stored for 30 minutes and then washed out thoroughly with water.

The color properties of the bleached hair strands were measured with the help of a Colorimeter of the Minolta Firm, Model Chroma-Meter II. The results are tabulated in Table I below.

TABLE I

MEASURED COLOR PROPERTIES OF BLEACHED NATURAL HAIR

|  | L | a | b |
| --- | --- | --- | --- |
| UNBLEACHED HAIR | 26.4 | 3.5 | 7.5 |
| HAIR BLEACHED WITH AGENT NR. 1 | 67.7 | 4.3 | 34.0 |
| HAIR BLEACHED WITH AGENT NR. 2 | 66.2 | 4.6 | 32.0 |
| HAIR BLEACHED WITH AGENT NR. 3 | 43.4 | 5.2 | 22.5 |

The hair strands treated with the bleaching agent (Nr. 1 and br. 2) according to the invention have a considerably higher brightness and considerably larger yellow spectrum value (b) both in comparison to the untreated hair strands and also to the hair strands bleached with the bleaching agent of German Patent Application DE-AS 20 23 922 (Nr. 3), which clearly shows that the bleaching composition according to the invention has improved bleaching action.

Unless otherwise indicated all percentages in the above specification are percentage by weight.

While the invention has been illustrated and described as embodied in a process for making a persulfate containing granulate for decolorizing or bleaching hair, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

What is claimed is:

1. A method of making a granulate composition for decolorizing or bleaching hair, said method consisting of the steps of:

a) preparing a powdery mixture consisting of from 30 to 65% by weight of at least one inorganic persulfate, from 1 to 20% by weight of a binding agent, said binding agent being selected from the group consisting of polyvinylpyrrolidone and polyethylene glycols having molecular weights from 200 to 10000, from 15 to 45% by weight of at least one salt selected from the group consisting of alkali metal carbonates, alkali metal hydrogen carbonates, alkali metal silicates; and alkaline earth metal carbonates, from 0.1 to 3 percent by weight of a chelating agent, and at least one auxiliary and additive substance selected from the group consisting of perfume oils, hair dyes, amphoteric surface-active substances, anionic surface-active substances, cationic surface-active substances, nonionic surface-active substances and water-soluble thickeners;

b) after the preparing of the powdery mixture, spraying an alcohol selected from the group consisting of ethanol, isopropanol and mixtures thereof into the powdery mixture to form a moistened mixture;

c) granulating the moistened mixture formed in the spraying of step b) in a granulating apparatus to form a moist granulate; and d) after the granulating of step c), drying the moist granulate to remove said alcohol and to form the granulate composition, wherein a weight ratio of said powdery mixture to said alcohol in the moistened mixture formed in step b) is from 13:1 to 4:1.

2. The method as defined in claim 1, wherein said granulate composition is made in 10 to 60 minutes.

3. Composition for decolorizing or bleaching hair made by mixing an aqueous hydrogen peroxide preparation containing from 4 to 18 percent by weight hydrogen peroxide and a granulate composition; said granulate composition being made by a method consisting of preparing a powdery mixture consisting of from 30 to 65% by weight of at least one inorganic persulfate, from 1 to 20% by weight of a binding agent, said binding agent being selected from the group consisting of polyvinylpyrrolidone and polyethylene glycols having molecular weights from 200 to 10000, from 15 to 45% by weight of at least one salt selected from the group consisting of alkali metal carbonates, alkali metal hydrogen carbonates, alkali metal silicates, and alkaline earth metal carbonates, from 0.1 to 3 percent by weight of a chelating agent, and at least one auxiliary and additive substance selected from the group consisting of perfume oils, hair dyes, amphoteric surface-active substances, anionic surface-active substances, cationic surface-active substances, nonionic surface-active substances and water-soluble thickeners; after making the powdery mixture, spraying an alcohol selected from the group consisting of ethanol, isopropanol and mixtures thereof into the powdery mixture to form a moistened mixture; granulating the moistened mixture formed in the spraying in a granulating apparatus to form a moist granulate; and after the granulating, drying the moist granulate to remove said alcohol and to form the granulate composition, wherein a weight ratio of said powdery mixture to said alcohol is from 13:1 to 4:1 in the moistened mixture and wherein said granulate composition and said hydrogen peroxide preparation are mixed in a weight ratio of said granulate compositing to said hydrogen peroxide preparation of 1:1 to 1:3.

4. The method as defined in claim 3, wherein said at least one inorganic persulfate is selected from the group consisting of sodium persulfate, potassium persulfate and ammonium persulfate.

5. The method as defined in claim 1, wherein said at least one salt is selected from the group consisting of sodium carbonate, magnesium carbonate, sodium hydrogen carbonate and sodium silicate.

6. The composition as defined in claim 3, wherein said at least one salt is selected from the group consisting of sodium carbonate, magnesium carbonate, sodium hydrogen carbonate and sodium silicate.

* * * * *